(12) United States Patent
Cardwell et al.

(10) Patent No.: US 9,447,052 B2
(45) Date of Patent: Sep. 20, 2016

(54) PROCESSES FOR PREPARING PYRIMIDINE COMPOUNDS

(75) Inventors: Kevin Stuart Cardwell, Stevenage (GB); Claire Frances Crawford, Stevenage (GB); Suzanne Helen Davies, Stevenage (GB); Charles Edward Wade, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 36 days.

(21) Appl. No.: 13/698,102

(22) PCT Filed: May 17, 2011

(86) PCT No.: PCT/US2011/036821
§ 371 (c)(1),
(2), (4) Date: Nov. 15, 2012

(87) PCT Pub. No.: WO2011/146494
PCT Pub. Date: Nov. 24, 2011

(65) Prior Publication Data
US 2013/0060028 A1    Mar. 7, 2013

Related U.S. Application Data

(60) Provisional application No. 61/345,224, filed on May 17, 2010.

(51) Int. Cl.
    C07D 239/70    (2006.01)
    C07C 227/08    (2006.01)
    C07C 229/16    (2006.01)

(52) U.S. Cl.
    CPC ........... *C07D 239/70* (2013.01); *C07C 227/08* (2013.01); *C07C 229/16* (2013.01)

(58) Field of Classification Search
    CPC . C07D 239/70; C07D 229/16; C07D 227/22
    USPC .......................................... 544/253; 560/122
    See application file for complete search history.

(56) References Cited

U.S. PATENT DOCUMENTS

| | | | | |
|---|---|---|---|---|
| 4,235,776 A * | 11/1980 | Kornfeld | .............. | C07D 237/30 548/515 |
| 4,277,465 A | 7/1981 | Kamada | | |
| 4,315,939 A * | 2/1982 | Frickel | .................. | C07C 271/22 514/318 |
| 4,352,800 A | 10/1982 | Kamada | | |
| 4,619,941 A * | 10/1986 | Wright, Jr. | ........... | C07D 231/12 514/397 |
| 6,503,745 B1 | 1/2003 | Chand et al. | | |
| 6,750,228 B1 | 6/2004 | Barta et al. | | |
| 7,232,902 B2 | 6/2007 | Mulholland et al. | | |
| 2004/0097525 A1 * | 5/2004 | Hickey | ............... | C07D 239/56 514/260.1 |

FOREIGN PATENT DOCUMENTS

| | | |
|---|---|---|
| GB | 986904 | 3/1965 |
| WO | WO99/24420 | 5/1999 |
| WO | WO00/66567 | 11/2000 |
| WO | WO 03/016287 A2 | 2/2003 |

OTHER PUBLICATIONS

Pfeiffer, et al. Liebigs Ann. Chem., 564-589 (1980).
A. Balog, "Some β-Dicarbonyl N-Protected Amino Acids and Model Dipeptides," Revue Roumaine de Chimie, vol. 15, pp. 1375-1390 (1970).
Staab, H.A., et al.: Darstellung Von Imidazoliden, Synthese von Amiden, Hydraziden Und Hydroxamseauren Nach Der Imidazolidmethode, chemische Berichte, VCH, vol. 95, Jan. 1, 1962, pp. 1275-1283, XP000994827, ISSN: 0009-2940.
Staab H, A.: Syntheses Using Heterocyclic Amides (azolides), Angewandte Chemie. International Edition, VCH Verlag, Weinheim, DE, vol. 1, No. 7, Jan. 1, 1962, pp. 351-367, XP000197451, ISSN: 0570-0833 DOI: 10.1002/ANIE.196203511 (See, e.g., p. 357 "Synthesis of Amides").
EPO Communication/EPOForm 1507s dated Oct. 23, 2013 including Supplementary European Search Report (EPO Form 1503) and European Search Opinion (Form 1703); 5 pages total.

* cited by examiner

*Primary Examiner* — James O Wilson
*Assistant Examiner* — Ebenezer O Sackey
(74) *Attorney, Agent, or Firm* — Loretta J. Sauermeich; Edward R. Gimmi

(57) ABSTRACT

This invention relates to methods of making a compound of formula (I) and intermediates for same

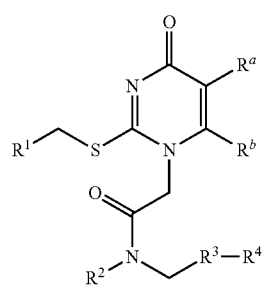

the compounds of formula (I) being useful for treating cardiovascular and inflammatory diseases such as atherosclerosis.

15 Claims, No Drawings

PROCESSES FOR PREPARING PYRIMIDINE COMPOUNDS

This application is a 371 of International Application No. PCT/US2011/036821, filed 17 May 2011, which claims the benefit of U.S. Provisional Application No. 61/345,224 filed 17 May 2010, which is incorporated herein in its entirety.

AREA OF THE INVENTION

The present invention relates to a process for the preparation of certain pyrimidinone compounds.

BACKGROUND

WO 01/60805 (SmithKline Beecham plc) discloses a novel class of pyrimidinone compounds, inter alia those substituted at N1.

The pyrimidinone compounds described in WO 01/60805 are inhibitors of the enzyme lipoprotein associated phospholipase $A_2$ (Lp-PLA$_2$) and as such are expected to be of use in therapy, in particular in the primary and secondary prevention of acute coronary events, for instance those caused by atherosclerosis, including peripheral vascular atherosclerosis and cerebrovascular atherosclerosis.

Several processes for the preparation of such pyrimidinone compounds are also disclosed in WO 01/60805, inter alia alkylation of the pyrimidinone nucleus. This process generally suffers from moderate yields due to the poor selectivity seen in the alkylation of the pyrimidinone nucleus. Preparation of such compounds is also disclosed in WO 03/16287. While this process achieves improved selectivity, it generally suffers from modest yield particularly in the disclosed regioselective step.

The present invention provides particularly advantageous processes, not hitherto disclosed, for the preparation of some of the pyrimidinone compounds disclosed in WO 01/60805.

SUMMARY OF THE INVENTION

In a first aspect the instant invention provides a process for preparing a compound of formula (I):

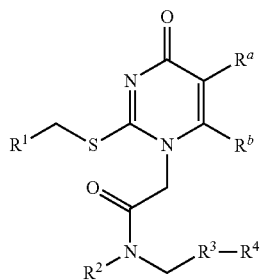

(I)

wherein:
$R^a$ and $R^b$ together with the pyrimidine ring carbon atoms to which they are attached form a cyclopentyl ring;
$R^1$ is phenyl, unsubstituted or substituted by 1-3 fluoro groups;
$R^2$ is $C_{(1-3)}$alkyl substituted by $NR^5R^6$; or
$R^2$ is Het-$C_{(0-2)}$alkyl in which Het is a 5- to 7-membered heterocyclic ring containing N and in which N may be substituted by $C_{(1-6)}$alkyl;
$R^3$ is phenyl;
$R^4$ is phenyl unsubstituted or substituted by $C_{(1-6)}$alkyl or mono to perfluoro-$C_{(1-4)}$alkyl; and
$R^5$ and $R^6$ which may be the same or different are $C_{(1-6)}$alkyl;

the process comprising carrying out one or more of the following reaction steps:

(a) treating a $C_{(1-4)}$alkyl 2-oxocyclopentanecarboxylate with an alkali metal salt of glycine to form a compound of formula (A)

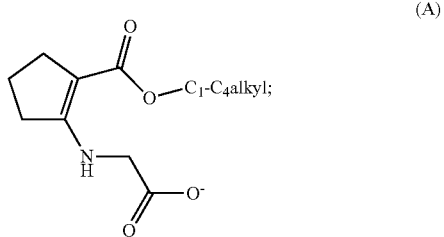

(A)

(b) cyclising a compound of formula (A) to form the hexahydro-1H-cyclopenta[d]pyrimidin-1-yl)acetic acid of formula (B)

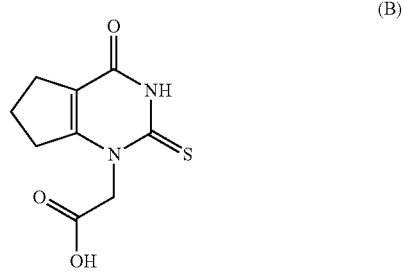 [SMILES: O=C(O)Cn1c2c(c(=O)[nH]c1=S)CCC2]

(B)

by treating a compound of formula (A) with either (i) or (ii):
(i) a thiocyanate salt and
  a) a haloalkylsilane and a proton source (such as water or alcohol), with heating, or
  b) an anhydrous acid, with heating; or
(ii) trimethylsilylisothiocyanate, with heating;

(c) forming a thio-4-oxo-4,5,6,7-tetrahydro-1H-cyclopenta[d]pyrimidin-1-yl)acetic acid of formula (C)

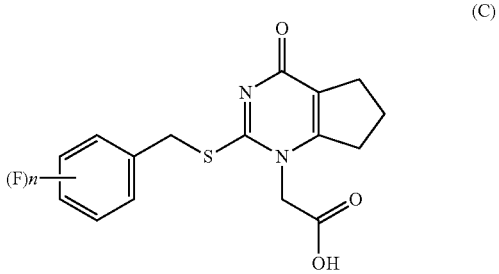

(C)

where n is 0 to 3,
by a treating compound of formula (B) with a thio-alkylating reagent which is a benzyl derivative of formula (D)

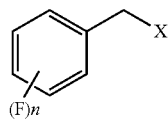

where n is 0 to 3 and X is a leaving group, in the presence of an alkali metal base and/or an alkali metal carbonate;

(d) treating an aldehyde of formula (E)

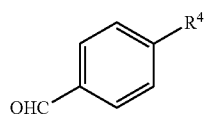

with an amine, a heavy metal catalyst and hydrogen to form a secondary amine of formula (F)

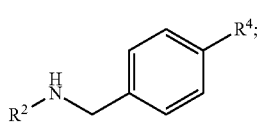

and (e) forming a compound of formula (I) by treating a compound of formula (C) with carbonyldiimidazole and the secondary amine of formula (F) and heating the mixture.

Also within the scope of this invention are the several intermediates used in the foregoing process for making compounds of formula (I), and processes of making such intermediates comprising one or more of the foregoing steps as indicated.

DETAILED DESCRIPTION OF THE INVENTION

For the purposes of this invention, $C_{(1-6)}$alkyl (which may be alternatively referred to as $(C_1-C_6)$alkyl, including, e.g., $C_{(1-4)}$alkyl or $C_1-C_4$ alkyl) refers to a straight- or branched-chain hydrocarbon radical having the specified number of carbon atoms. For example, as used herein, the terms "$C_{(1-6)}$-alkyl" refers to an alkyl group having at least 1 and up to 6 carbon atoms. Examples of such branched or straight-chained alkyl groups include, but are not limited to, methyl, ethyl, n-propyl, isopropyl, isobutyl, n-butyl, t-butyl, n-pentyl, isopentyl, and n-hexyl, and branched analogs of the latter 3 normal alkanes.

Halo refers to fluoro, bromo, chloro or iodo. Where such a moiety is on an alkyl group, there may be 1 or more of any one of these four halo groups, or mixtures of them.

When the term "mono to perfluoro-$C_{(1-4)}$alkyl" is used it refers to an alkyl group having at least 1 and up to 4 carbon atoms that is substituted with at least one fluoro group on any or all of the carbons, and may have up to 2n+1 fluoro groups where n is the number of carbons. Examples include, but are not limited to, fluoromethyl, difluoromethyl, trifluoromethyl, 2,2,2-trifluoroethyl, pentafluoroethyl, 2-(trifluoromethyl)ethyl, and nonafluoro-tert-butyl. Trifluoromethyl is a particularly useful group, especially when present at the 4 position on the $R^4$ phenyl ring.

With regards to the phenyl of $R^1$, if it is substituted by fluoro there may be 1-3 fluoro groups on the phenyl ring at any combination of positions on the ring. Particularly useful are the 4-fluorophenyl, 3,4-difluorophenyl, 3,4,5-trifluorophenyl, or 2,3-difluorophenyl groups, more particularly the 4-fluorophenyl, 3,4,5-trifluorophenyl, or 2,3-difluorophenyl groups.

In regard to $R^2$, suitable 5- to 7-membered heterocyclic rings containing N include pyrrolidine, piperidine and azepane.

$C_{1-6}$ (e.g. $C_{1-4}$) alcohols include branched or straight-chained alkanes having at least 1 and up to 6 carbons, and substituted by 1, 2 or 3 —OH groups. Examples include, but are not limited to, methyl, ethyl, n-propyl, isopropyl, isobutyl, n-butyl, t-butyl, n-pentyl, isopentyl, and n-hexyl alcohols, and branched analogs thereof.

In some embodiments, the process is carried out in accordance with the following description.

In step (a), alkyl esters of 2-oxocyclopentanecarboxylate are available commercially. The methyl ester is particularly useful and readily available. The alkali metal salt of glycine may be the sodium, potassium or lithium salt, which are available commercially or prepared in situ from glycine and a suitable base such as sodium ethoxide. The sodium salt is particularly useful. The reaction is run in a polar solvent such as a low molecular weight aqueous alcohol (e.g. $C_{1-4}$, e.g. ethanol, methanol, and/or isopropanol), an amidic solvent (e.g. N-methylpyrrolidinone) or a carboxylic acid (e.g. acetic acid). The reaction mixture is heated, e.g., to between 50°-70° C. for a sufficient, generally short time, e.g. a couple of hours or so, and is then worked up by conventional means to obtain the alkali metal salt of ({2-[(methyloxy)carbonyl]-1-cyclopenten-1-yl}amino)methyl ester or used in solution as is.

With regards to the cyclization step (b), making the hexahydro-1H-cyclopenta[d]pyrimidin-1-yl)acetic acid of formula (B), the alkali metal salt of formula (A) is treated with either:

(i) a thiocyanate salt such as ammonium thiocyanate or an alkali metal thiocyanate such as sodium thiocyanate, or potassium thiocyanate, and a) a haloalkylsilane and a proton source such as water or alcohol (e.g., $C_{1-4}$ alcohols, including e.g., methanol) in an appropriate solvent, such as an amidic solvent (e.g. N-methylpyrrolidinone) or a carboxylic acid (e.g. acetic acid), for a sufficient time, generally several hours, at elevated temperature such as between 80°-120° C.; or b) an anhydrous acid (inorganic or organic) such as anhydrous hydrochloric acid or methane sulfonic acid, with heating (such as in (a) above); or (ii) trimethylsilylisothiocyanate, with heating (such as in (i) above).

Methods using the thiocyanate salt are particularly suitable. In such methods, treatment with the thiocyanate salt will generally be followed by treatment with the haloalkylsilane and proton source, or with anhydrous acid, although the reagents may be combined in any order. By any of the cyclization methods, after applying heat to the mixture, generally for several hours, it is cooled and the product isolated and purified by conventional means.

The thiol of formula (C) [step (c)] is prepared by treating the hexahydro-1H-cyclopenta[d]pyrimidin-1-yl)acetic acid with a thio-alkylating agent which is an unsubstituted or substituted benzyl moiety of formula (D). Formula (D) can have any suitable leaving group (X) which is exemplified by Cl, Br, I or an —OSO$_2$R group where R is alkyl (e.g., $C_{1-6}$), perfluoroalkyl (e.g. trifluoromethyl) or an aromatic group (e.g. phenyl). Acid (B) is stirred in a suitable polar solvent, for example water and a low molecular weight alcohol, and then treated with organic or inorganic base. For example, an alkali metal base such as NaOH or KOH and/or an alkali metal carbonate such as $Na_2CO_3$ or $K_2CO_3$ is added. This mixture is maintained or heated at low temperature, e.g. 20°-50° C. and the benzyl derivative is added and heating is continued for a suitable time, generally a couple of hours. The product is recovered by conventional means; addition of a low molecular weight organic or inorganic acid (e.g., formic, sulphuric or phosphoric acid) may facilitate crystallization.

In step (d), the secondary amine (F) needed to form the amide group in formula (I) is prepared from an aldehyde (E) by treating the aldehyde with the appropriate substituted amine in the presence of a heavy metal catalyst such as palladium and hydrogen gas, in an appropriate solvent such as an aromatic solvent (e.g. toluene), a ketonic solvent (e.g. methylisobutylketone) or an alkyl acetate solvent (e.g. isopropyl acetate). Suitable amines are alkylene diamines of the formula $(C_{1-3})NR^5R^6$, where $R^5$ and $R^6$ are as defined in formula (I), and of the formula Het-$C_{(0-2)}$alkyl in which Het is a 5- to 7-membered heterocyclic ring containing N and in which N may be substituted by $C_{(1-6)}$ alkyl. When hydrogenation is completed, the product is recovered by conventional means (it may be left and used in solution).

The last step, step (e) will typically comprise treating compound (C) with carbonyldiimidazole in an aprotic solvent, then combining the mixture with the amine (F) and heating the mixture. Thus, step (e) is suitably effected by first treating the thiol (C) prepared in step (c) with carbonyldiimidazole in an appropriate aprotic solvent such as an aromatic solvent (e.g. toluene), a ketonic solvent (e.g. methylisobutylketone) or $C_{1-6}$ alkyl acetate solvent (e.g. isopropyl acetate) and heating the solution. Alternatively, thiol (C) may be combined with the reagents in any order. This step forms an imidazole intermediate that is not isolated, but added as is to a solution of the secondary amine (F) prepared in step (d). This solution is heated to e.g., 80°-100° C. or thereabout until conventional testing shows the reaction has gone to completion. Product is isolated by conventional means. In alternative embodiments, the imidazole intermediate may be isolated for subsequent reaction with amine (F). It has been found that combined use of the carbonyldiimidazole and amine in this step desirably reduces or removes residual thio-alkylating agent (e.g. (D)) in the thiol (C) (in some embodiments, to less than 1 ppm (D)). In some embodiments, methanol is used as a solvent during isolation of the product and may improve yield and/or purity. The present invention encompasses a methanol solvate of compounds of formula (I), formed by isolation comprising the use of methanol as a solvent.

In one aspect, the invention relates to novel compounds of formula (A). In another aspect, the invention relates to a method of preparing a compound of formula (A), comprising the aforementioned step (a).

In another aspect, the invention relates to novel compounds of formula (B). In another aspect, the invention relates to a method of preparing a compound of formula (B), comprising the aforementioned steps (a) and (b).

In another aspect, the invention relates to a method of preparing a compound of formula (C), comprising the aforementioned steps (a), (b) and (c).

In another aspect, the invention relates to a method of preparing a compound of formula (I), comprising the aforementioned steps (a)-(c).

In another aspect, the invention relates to a method of preparing a compound of formula (I), comprising the aforementioned steps (a)-(e).

All publications (including but not limited to published patent applications and patents) referred to herein are incorporated by reference in their entirety.

EXAMPLES

Example 1

Preparation of Sodium ({2-[(Methyloxy)carbonyl]-1-cyclopenten-1-yl}amino)acetate

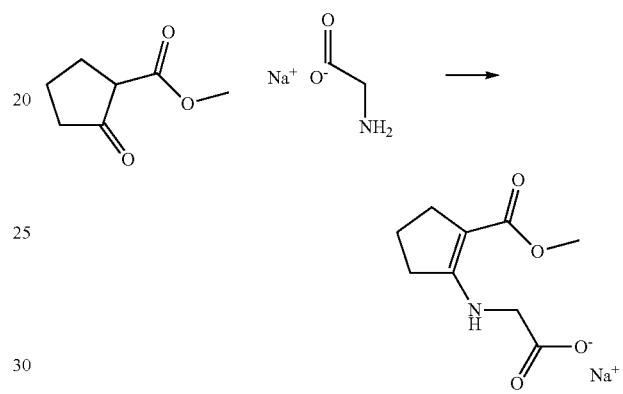

Glycine sodium salt (69.64 g, 1.02 eq) and industrial methylated spirits ("IMS") (800 mL), a grade of denatured ethanol, were combined and stirred. Then water (40 mL) was added to the slurry. Methyl oxocyclopentanone carboxylate (100 g, 1.00 eq) was then added and the slurry heated to 60° C.±3° C. After 2 hrs the slurry was cooled to 20° C.±3° C. over 40 min, aged for 30 min then filtered. The cake was washed with industrial methylated spirits (2×200 mL), deliquored, then dried further at 70° C. in an oven under reduced pressure to yield the title compound as a white solid (139.8 g, 89%).

$^1$H NMR ($d_4$ MeOD) δ 1.80 (2H, quintet), 2.49 (2H, t), 2.56 (2H, t), 3.63 (3H, s), 3.75 (2H, s).

Example 2

Preparation of (4-Oxo-2-thioxo-2,3,4,5,6,7-hexahydro-1H-cyclopenta[d]pyrimidin-1-yl)acetic acid

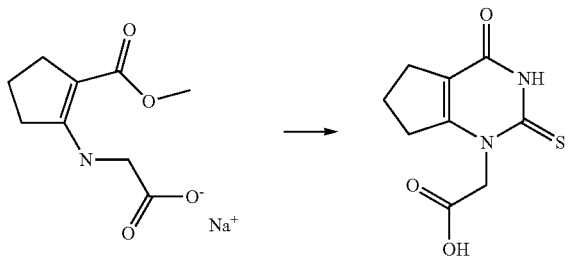

Sodium ({2-[(Methyloxy)carbonyl]-1-cyclopenten-1-yl}amino)acetate (60 g) and sodium thiocyanate (26.6 g) were stirred in N-methylpyrrolidinone (240 ml) and water (2.94 ml) under a nitrogen atmosphere. Chlorotrimethylsilane (73.8 g) was added and the mixture heated to 117±3° C. After 3 hours at this temperature the reaction mixture was cooled to 90° C. and water (480 ml) was added. The mixture was cooled to 2° C. and the product isolated by filtration. It was washed with water (2×120 ml) then acetone (2×60 ml) and dried at 60° C. in an oven under reduced pressure to yield the title compound as an off-white solid (50.69 g, 83%). $^1$H NMR (d$_6$ DMSO) δ 2.00 (2H, quintet), 2.60 (2H, t), 2.87 (2H, t), 4.95 (2H, broad s), 12.57 (1H, broad s), 13.26 (1H, broad s).

Example 3

Alternative Method for Making (4-Oxo-2-thioxo-2,3,4,5,6,7-hexahydro-1H-cyclopenta[d]pyrimidin-1-yl)acetic acid

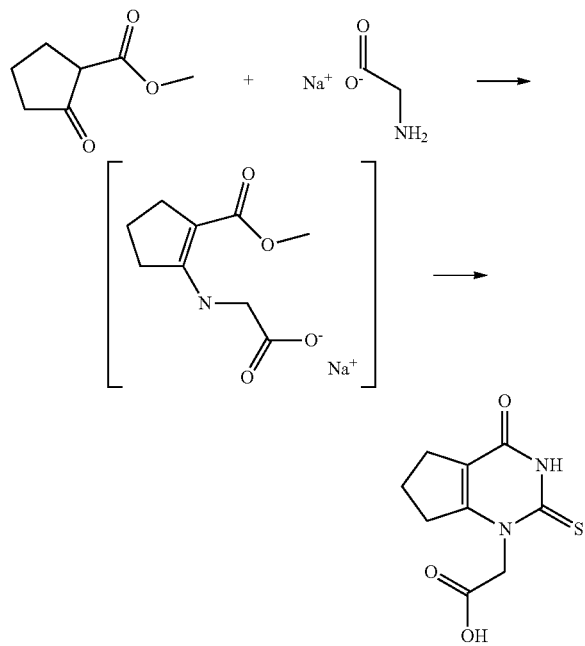

Methyl 2-oxocyclopentanecarboxylate (750 g) was added to a stirred suspension of glycine, sodium salt (528 g) in N-methylpyrrolidinone (4 L) under a nitrogen atmosphere at 60±3° C. over 45 minutes. The ester was washed in with a further portion of N-methylpyrrolidinone (1.3 L) and the mixture was stirred at this temperature for 2 hours. The mixture was then cooled to 20±3° C. and sodium thiocyanate (599 g) was added. Chlorotrimethylsilane (2.01 kg) was added over 45 minutes and the reaction mixture was heated with a jacket set to raise the temperature to 123° C. over 45 minutes. During this heating up period, the reaction mixture became thicker and some volatiles were distilled out. The temperature of the reaction mixture rose to 117±3° C. This reaction temperature was maintained for 3 hours. The reaction mixture was cooled to 90±3° C. Water (10.5 L) was added and the suspension was cooled to 2±3° C. over 4 hours and the product was collected by filtration. The product was washed twice with water (2×2.3 L) and twice with acetone (2×1.2 L) and dried in vacuo at 60° C. to yield the title compound as an off-white solid (920 g, 77%); $^1$H NMR (d$_6$ DMSO) δ 2.00 (2H, quintet), 2.60 (2H, t), 2.87 (2H, t), 4.95 (2H, broad s), 12.57 (1H, broad s), 13.26 (1H, broad s).

Example 4

Preparation of (2-{[(4-Fluorophenyl)methyl]thio}-4-oxo-4,5,6,7-tetrahydro-1H-cyclopenta[d]pyrimidin-1-yl)acetic acid

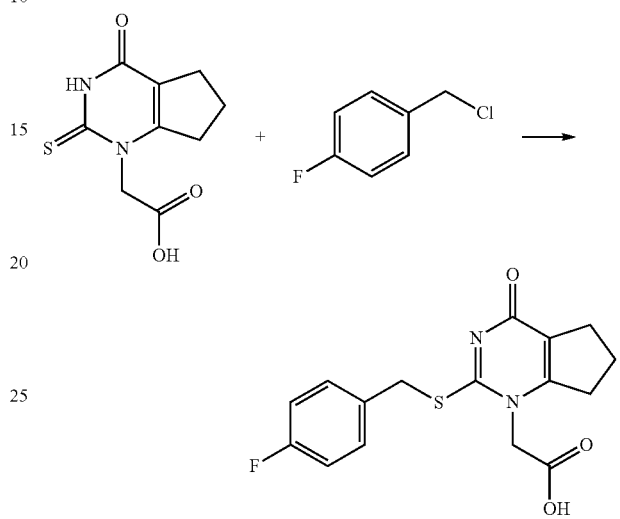

(4-oxo-2-thioxo-2,3,4,5,6,7-hexahydro-1H-cyclopenta[d]pyrimidin-1-yl)acetic acid (30.0 g, 1.0 eq) was slurried in a mixture of water (162 mL) and isopropyl alcohol (30 mL). KOH solution (50% aqueous, 28.3 g, 1.90 eq) was added followed by a water line wash (15 mL) resulting in a solution. Then K$_2$CO$_3$ (2.75 g, 0.15 eq) was charged and the solution was heated to 40±3° C. Thereafter 4-fluorobenzyl chloride (18.2 g, 0.95 eq) was added, followed by a line wash of isopropyl alcohol (18 mL) and the reaction mixture was stirred at 40±3° C. until the reaction was deemed complete (~2.5 hours). The reaction mixture was cooled to 20±3° C. and formic acid (3.1 g, 0.5 eq) was added resulting in crystallisation of the product within 30 minutes. A second charge of formic acid (10.4 g, 1.7 eq) was added over 1 hour and the slurry was stirred at 20±3° C. for at least one hour. The slurry was filtered to isolate the product, which was washed twice with a mixture of water (48 mL) and isopropyl alcohol (12 mL), then with isopropyl alcohol (60 mL) and dried in vacuo at 50° C. to yield the title compound as an off-white solid (40.6 g, 92%). $^1$H NMR (d$_6$ DMSO) δ 1.95 (2H, m), 2.57 (2H, t), 2.85 (2H, t), 4.4 (2H, s), 4.7 (2H, s), 7.15 (2H, dd), 7.45 (2H, dd), ~13.6 (1H, vbrs).

Example 5

Preparation of N,N-diethyl-N'-{[4'-(trifluoromethyl)-4-biphenylyl]methyl}-1,2-ethanediamine

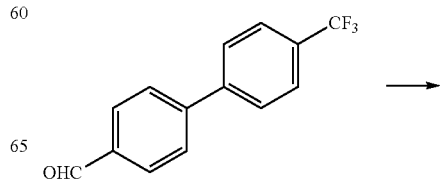

-continued

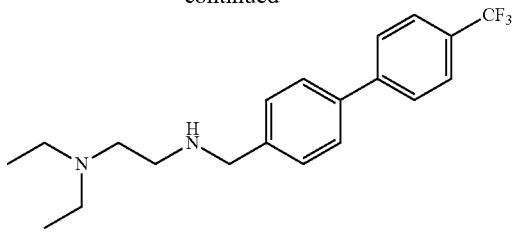

A mixture of 4'-(trifluoromethyl)-4-biphenylcarbaldehyde, (43.6 kg, 1.1 eq., see WO 01/60805), N,N-diethylethylenediamine (21.2 kg, 1.15 equiv.) and 5% palladium on charcoal (Degussa E101 N/W, 50% wet paste, 1.7 kg) in toluene (138 Kg) was hydrogenated at 20±3° C. and 50 psi until completion. The reaction mixture was filtered and the catalyst bed washed with toluene (2×36.7 kg). The solution was washed with water (84.8 kg) and concentrated under reduced pressure to ca. 85 L. This concentrate was used in the next step, Example 6, without further purification.

Example 6

Preparation of N-[2-(diethylamino)ethyl]-2-(2-{[(4-fluorophenyl)methyl]thio}-4-oxo-4,5,6,7-tetrahydro-1H-cyclopenta[d]pyrimidin-1-yl)-N-{[4'-(trifluoromethyl)-4-biphenylyl]methyl}acetamide

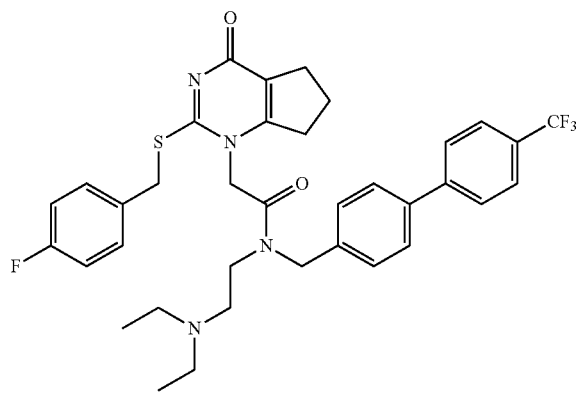 [SMILES: CCN(CC)CCN(Cc1ccc(-c2ccc(C(F)(F)F)cc2)cc1)C(=O)Cn1c(SCc2ccc(F)cc2)nc(=O)c2c1CCC2]

6a. A stirred slurry of carbonyldiimidazole (30.9 kg, 1.2 equiv.) in methylisobutylketone (255 kg) under nitrogen was heated to 70±3° C. (2-{[(4-fluorophenyl)methyl]thio}-4-oxo-4,5,6,7-tetrahydro-1H-cyclopenta[d]pyrimidin-1-yl) acetic acid (53.0 kg) was added in a portionwise manner and the mixture stirred at 70±3° C. until no starting material remained.

6b. The suspension of imidazolide intermediate from 6a was added to a solution N,N-diethyl-N'-{[4'-(trifluoromethyl)-4-biphenylyl]methyl}-1,2-ethanediamine (see Example 5), washing in with methylisobutylketone (43 kg). The mixture was heated to 92±3° C. until complete conversion to the title compound was established. The reaction mixture was concentrated under reduced pressure to ca. 240 L and then cooled to 40 to 45° C. prior to the addition of methanol (105 kg). The solution was cooled to 20 to 25° C. to give a slurry, which was then heated to 50° C. and held for 30 mins. The slurry was cooled to 2±3° C. at 0.3° C./min and held for a further 30 mins. The product was isolated by filtration and washed with cold methanol (5±3° C., 2×168 kg) before being dried under reduced pressure at 47±3° C. to yield the title compound, intermediate grade as an off-white solid (97.4 kg uncorrected for methanol; 90.9 kg corrected for methanol, 86%). $^1$H NMR (CDCl$_3$, ca 1.9:1 rotamer mixture) δ 0.99 (6H, t), 2.10 (2H, m), 2.50 (4H, q), 2.58/2.62 (2H, 2×t), 2.70/2.82 (2H, 2×t), 2.86 (2H, t), 3.28/3.58 (2H, 2×t), 4.45/4.52 (2H, 2×s), 4.68/4.70 (2H, 2×s), 4.61/4.93 (2H, s), 6.95 (2H, m), 7.31 (2H, d), 7.31/7.37 (2H, 2×m), 7.48/7.52 (2H, d), 7.65 (2H, m), 7.72 (2H, m).

Example 7

Alternative method for making (2-{[(4-Fluorophenyl)methyl]thio}-4-oxo-4,5,6,7-tetrahydro-1Hcyclopenta[d]pyrimidin-1-yl)acetic acid (4-oxo-2-thioxo-2,3,4,5,6,7-hexahydro-1H-cyclopenta[d]pyrimidin-1-yl)acetic acid (20.0 g, 1.0 eq) was slurried in a mixture of water (112 mL) and isopropyl alcohol (20 mL). NaOH solution (50.9% aqueous, 13.82 g, 1.99 eq) was added followed by a water line wash (10 mL) resulting in a solution. Then Na$_2$CO$_3$ (1.50 g, 0.16 eq) was charged and the solution was heated to 40±3° C. Thereafter 4-fluorobenzyl chloride (13.4 g, 1.05 eq) was added, followed by a line wash of isopropyl alcohol (12 mL) and the reaction mixture was stirred at 40±3° C. until the reaction was deemed complete (~2.5 hours). The reaction mixture was cooled to 20±3° C. and formic acid (2.4 g, 0.6 eq) was added resulting in crystallisation of the product within 30 minutes. A second charge of formic acid (6.9 g, 1.7 eq) was added over 1 hour and the slurry was stirred at 20±3° C. for at least one hour. The slurry was filtered to isolate the product, which was washed twice with a mixture of water (32 mL) and isopropyl alcohol (8 mL), then with isopropyl alcohol (40 mL) and dried in vacuo at 50° C. to yield the title compound as an off-white solid (28.6 g, 97% th). $^1$H NMR (d$_6$ DMSO) δ 1.95 (2H, m), 2.57 (2H, t), 2.85 (2H, t), 4.4 (2H, s), 4.7 (2H, s), 7.15 (2H, dd), 7.45 (2H, dd), ~13.6 (1H, vbrs).

These examples are given to illustrate the invention, not to limit it. What is reserved to the inventors can be determined by reference to the claims below.

What is claimed is:
1. A process for making a compound of formula (I):

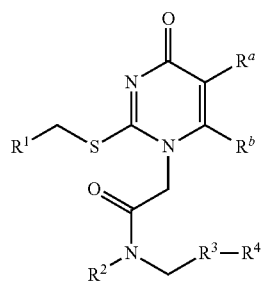

wherein:
R$^a$ and R$^b$ together with the pyrimidine ring carbon atoms to which they are attached form a cyclopentyl ring;
R$^1$ is phenyl, unsubstituted or substituted by 1 to 3 fluoro groups;
R$^2$ is C$_{(1-3)}$alkyl substituted by NR$^5$R$^6$; or
R$^2$ is Het-C$_{(0-2)}$alkyl in which Het is a 5- to 7- membered heterocyclic ring containing N and in which N may be substituted by C$_{(1-6)}$alkyl;

$R^3$ is phenyl;
$R^4$ is phenyl unsubstituted or substituted by $C_{(1-6)}$alkyl or mono to perfluoro-$C_{(1-4)}$alkyl; and
$R^5$ and $R^6$ which may be the same or different are $C_{(1-6)}$alkyl;

the process comprising:
(a) treating a $C_{(1-4)}$alkyl 2-oxocyclopentanecarboxylate with an alkali metal salt of glycine to form a compound of formula (A)

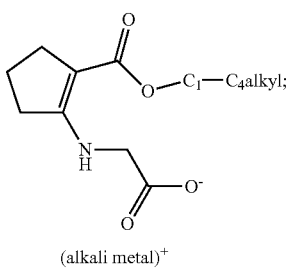

(A)

(b) cyclising a compound of said formula (A) to form the hexahydro-1H-cyclopenta[d]pyrimidin-1-yl)acetic acid of formula (B)

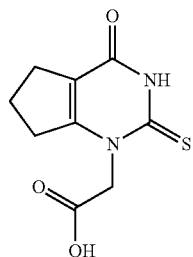

(B)

by treating a compound of said formula (A) with either:
(i) a thiocyanate salt and
  a) a haloalkylsilane and a proton source, with heating, or
  b) an anhydrous acid, with heating; or
(ii) trimethylsilylisothiocyanate, with heating;
  (c) forming a thio-4-oxo-4,5,6,7-tetrahydro-1H-cyclopenta [d]pyrimidin-1-yl)acetic acid of formula (C)

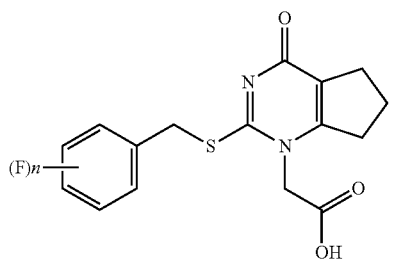

(C)

where n is 0 to 3,
by treating a compound of said formula (B) with a thioalkylating reagent which is a benzyl derivative of formula (D)

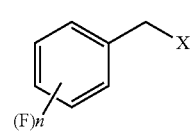

(D)

where n is 0 to 3 and X is a leaving group, in the presence of an alkali metal base and/or an alkali metal carbonate; and
(d) forming a compound of formula (I) by treating a compound of said formula (C) with carbonyldiimidazole and the secondary amine of formula (F)

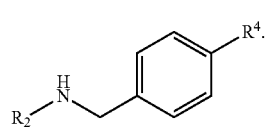

(F)

and heating the mixture.

2. The process according to claim 1, wherein said compound of formula (A) is treated with a thiocyanate salt, a haloalkylsilane and a proton source, with heating, to form the compound of formula (B).

3. The process according to claim 1, wherein the thiocyanate salt is ammonium thiocyanate or alkali metal thiocyanate.

4. The process according to claim 2, wherein the thiocyanate salt is ammonium thiocyanate or alkali metal thiocyanate.

5. The process according to claim 1, wherein the compound of formula (I) is isolated using methanol as a solvent.

6. A methanol solvate of a compound of formula (I) as defined in claim 1.

7. The process according to claim 1, wherein the compound of formula (A), $C_1$-$C_4$ alkyl is methyl.

8. A process for making N-[2-(diethylamino)ethyl]-2-(2-{[(4-fluorophenyl)methyl]thio}-4-oxo-4,5,6,7-tetrahydro-1H-cyclopenta[d]pyrimidin-1-yl)-N-{[4'-(trifluoromethyl)-4-biphenyly]methyl}acetamide:

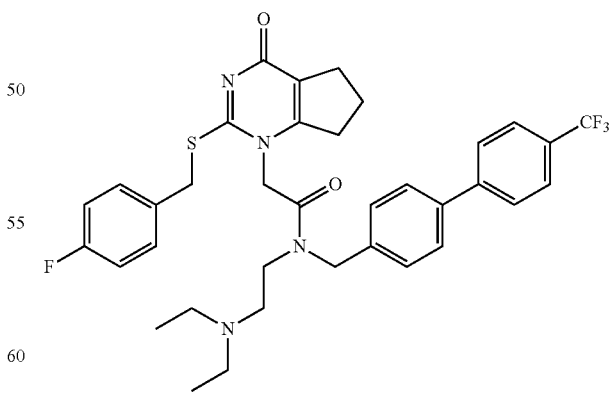

comprising:
treating a $C_{(1-4)}$alkyl 2-oxocyclopentanecarboxylate with an alkali metal salt of glycine to form a compound of formula (A)

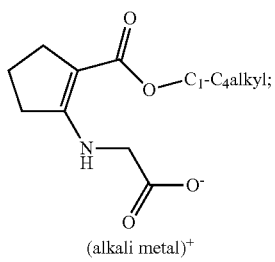

(A)

(b) cyclising the compound of formula (A) to form (4-oxo-2-thioxo-2,3,4,5,6,7-hexahydro-1H-cyclopenta[d]pyrimidin-1-yl)acetic acid:

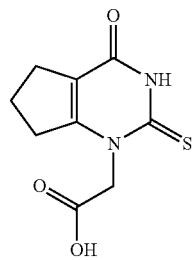 [SMILES: O=C(O)Cn1c2c(c(=O)[nH]c1=S)CCC2]

by treating the compound of formula (A) with either:
(i) a thiocyanate salt and
    a) a haloalkylsilane and a proton source, with heating, or
    b) an anhydrous acid, with heating; or
(ii) trimethylsilylisothiocyanate, with heating;
(c) forming (2-{[(4-fluorophenyl)methyl]thio}-4-oxo-4,5,6,7-tetrahydro-1H-cyclopenta[d]pyrimidin-1-yl)acetic acid:

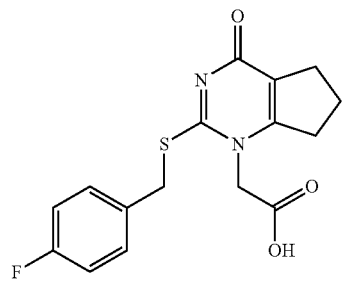 [SMILES: O=C(O)Cn1c(SCc2ccc(F)cc2)nc(=O)c2c1CCC2]

by treating (4-oxo-2-thioxo-2,3,4,5,6,7-hexahydro-1H-cyclopenta[d]pyrimidin-1-yl)acetic acid with a thio-alkylating reagent which is a benzyl derivative of formula (D):

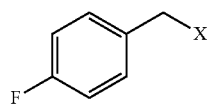

(D)

where X is a leaving group, in the presence of an alkali metal base and/or an alkali metal carbonate; and (d) forming N-[2-(diethylamino)ethyl]-2-(2-{[(4-fluorophenyl)methyl]thio}-4-oxo-4,5,6,7-tetrahydro-1H-cyclopenta[d]pyrimidin-1-yl)-N-{[4'-(trifluoromethyl)-4-biphenylyl]methyl}acetamide by treating the (2-{[(4-fluorophenyl)methyl]thio}-4-oxo-4,5,6,7-tetrahydro-1H-cyclopenta[d]pyrimidin-1-yl)acetic acid with carbonyldiimidazole and N,N-diethyl-N'-{[4'-(trifluoromethyl)-4-biphenylyl]methyl}-1,2-ethanediamine:

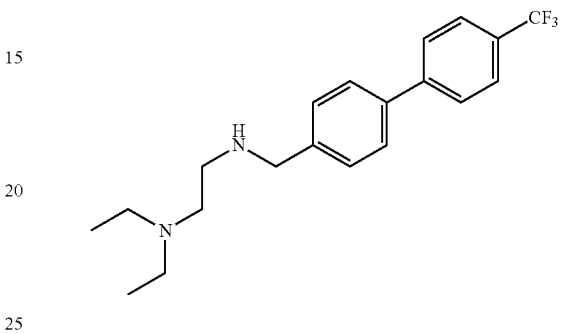

and heating the mixture.

9. The process according to claim 8, wherein said compound of formula (A) is treated with a thiocyanate salt, a haloalkylsilane and a proton source, with heating, to form (4-oxo-2-thioxo-2,3,4,5,6,7-hexahydro-1H-cyclopenta[d]pyrimidin-1-yl)acetic acid.

10. The process according to claim 8, wherein the thiocyanate salt is ammonium thiocyanate or alkali metal thiocyanate.

11. The process according to claim 9, wherein the thiocyanate salt is ammonium thiocyanate or alkali metal thiocyanate.

12. The process according to claim 8, wherein the compound of formula (A), $C_1$-$C_4$ alkyl is methyl.

13. The process according to claim 8, wherein the N-[2-(diethylamino)ethyl]-2-(2-{[(4-fluorophenyl)methyl]thio}-4-oxo-4,5,6,7-tetrahydro-1H-cyclopenta[d]pyrimidin-1-yl)-N-{[4'-(trifluoromethyl)-4-biphenylyl]methyl}acetamide is isolated using methanol as a solvent.

14. A methanol solvate of N-[2-(diethylamino)ethyl]-2-(2-{[(4-fluorophenyl)methyl]thio}-4-oxo-4,5,6,7-tetrahydro-1H-cyclopenta[d]pyrimidin-1-yl)-N-{[4'-(trifluoromethyl)-4-biphenylyl]methyl}acetamide.

15. The process according to claim 8, wherein the compound of formula (D) is 4-fluorobenzyl chloride:

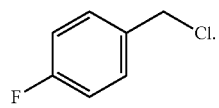

* * * * *